United States Patent
Grogl et al.

(12)

(10) Patent No.: US 6,284,739 B1
(45) Date of Patent: Sep. 4, 2001

(54) ANTILEISHMANIAL COMPOSITION FOR TOPICAL APPLICATION

(76) Inventors: Max Grogl, 3404 TanTerra Cir., Brookeville, MD (US) 20853; Lawrence Fleckenstein, 1809 Flanigan Ct., Iowa City, IA (US) 52246; Patrick McGreevy, 11526 Colt Terr., Silver Spring, MD (US) 20902; Brian Schuster, 1620 Crowell Rd., Vienna, VA (US) 22182

( * ) Notice: Subject to any disclaimer, the term of this patent is extended or adjusted under 35 U.S.C. 154(b) by 0 days.

(21) Appl. No.: 08/204,999

(22) Filed: Mar. 3, 1994

(51) Int. Cl.[7] ...................................................... A61K 31/70
(52) U.S. Cl. ................... 514/40; 514/38; 514/39
(58) Field of Search ................................ 514/39, 40, 38; 536/13.3, 13.6

(56) References Cited

U.S. PATENT DOCUMENTS 4,505,901 * 3/1985 El-On et al. ............................ 514/38
4,883,659 * 11/1989 Goodman et al. ..................... 424/78

* cited by examiner

*Primary Examiner*—Elli Peselev
(74) *Attorney, Agent, or Firm*—Elizabeth Arwine; John Francis Moran; Charles H. Harris

(57) ABSTRACT

The instant invention provides compositions containing as active agents paromomycin in combination with gentamicin. When given in combination, the compositions appear much more effective than when given alone. Furthermore, the compositions of the invention were found to be effective against several species of Leishmania that were not effectively inhibited by the prior art compositions.

14 Claims, No Drawings

ANTILEISHMANIAL COMPOSITION FOR TOPICAL APPLICATION

FIELD OF THE INVENTION

This invention relates to a means of effectively inhibiting leishmania infections by topical application of compositions containing paromomycin and gentamicin.

BACKGROUND OF THE INVENTION

Leishmania species are hemoflagellate protozoa which are transmitted by the bite of the sandfly. In man, the organisms grow and multiply in tissues of the reticuloendothelial system. Some of these species of parasites of genus Leishmania cause cutaneous lesions which usually appear as chronic, ulcerative skin lesions. Dermotropic species like *L. tropica, L. aethiopica,* and *L. major* are most prevalent in the Old World, while *L. peruviana, L. mexicana, L. guvanensis, L. amazonensis, L. panamensis,* and *L. braziliensis* are found in the New World. *L. panamensis* and *L. braziliensis* may metastasize to the oral-nasal mucosa to cause mucosal leishmaniasis. Both *L. aethiopica* and *L. mexicana* cause diffuse cutaneous leishmaniasis. No vaccine or other prophylaxis against these diseases is currently available.

Drugs most commonly used against these parasites contain the pentavalent antimony. The sodium stilbogluconate (Pentostam) and the meglumine antimonate (Glucantime) are commonly used. These drugs are toxic to the liver, kidneys, pancreas and heart. The most serious effects are pancreatitis and cardiac arrhythmias. Amphotericin B and Pentamidine are also used, but are equally toxic. Ketoconazole is effective against some species. The present treatment of choice required injections of pentavalent antimonies for 10–28 days under hospital care, since such treatment often results in side effects such as cardiac arrhythmias, pancreatitis and hepatitis.

U.S. Pat. No. 4,595,901 to El-On, et al. discloses a composition containing a mixture of paromomycin or a salt thereof with dimethylsulfoxide or quaternary ammonium salts, especially methylbenzethonium chloride. These compositions are effective against some Leishmania species, but are ineffective against others. The compositions of that patent have been found to be essentially ineffective against most New World strains and against some of the Old World strains. Gentamicin was tried in some of the El-On compositions, but was essentially ineffective when formulated in accord with the teaching of El-On. The claimed compositions of El-On are toxic to many patients when given at therapeutic levels.

DESCRIPTION OF THE INVENTION

The instant invention provides compositions containing as active agents paromomycin in combination with gentamicin. It is possible to ameliorate the effect of leishmaniasis by administration of compositions of the invention to patients suffering from leishmaniasis. When given in combination, the compositions appear much more effective than when given alone or with other ammonium salts such as those taught by El-On. Furthermore, the compositions of the invention were found to be effective against several species of Leishmania that were not effectively inhibited by the prior art compositions. At therapeutic levels, no toxic effects were seen in the animals treated with the compositions of the invention, while treatment using compositions of El-On in accord with the teachings of El-On resulted in toxic side effects in the animals.

The compositions of the invention contain as active agents an antileishmania-effective amount of paromomycin or a salt thereof and a paromomycin-potentiating effective amount of gentamicin. In a preferred embodiment, the active agents used in the compositions are in amounts of up to 40% paromomycin and up to 5% gentamicin in a carrier to provide a composition appropriate for topical application. Carriers used must be nontoxic. Addition of penetration agents was also found to be beneficial. Several of the commercially available carriers, including Aquaphilic, Aquacide, Aquaphor, Unibase and PEG base were found to be effective, as were some nonionic emulsion basis. Addition of known penatrants such as urea was also useful. In a preferred composition, the commercial product known as AQUAPHILIC was used with 10% urea added as a penetrant. The compositions of the invention proved to be particularly effective against both Old World and New World species of Leishmania. The gentamicin appears to act as a potentiation agent, enhancing the effect of the paromomycin. The gentamicin also acts as a bacteriostatic and bacteriocidal agent. The synergistic effect of the combination of active agents has not previously been known. The compositions of the invention can prevent progression of the papule into a full-blown lesion and are effective eradicating existing lesions.

The compositions have also been found to be especially effective in treatment of diffuse cutaneous leishmaniasis caused by *L. aethiopic* and *L. mexicana* and in treating and preventing metastasis of *L. panamensis* and *L. braziliensis* to the oral-nasal mucosa.

MATERIALS AND METHODS

The four species of Leishmania selected for testing were *L. major* (Strain Code MHOM/SU/74/WR779, *L. amanzonensis* (Strain Code MHOM/BR/73/WR669), *L. panamensis* (Strain Code MHOM/CR/87/WR746) and *L. mexicana* (Strain Code MHOM/US/90/WR972-B). *L. major* is an Old World species, while the other strains are New World species.

Animals used included Balb/c mice and C3He mice. (See table A) Balb/c mice were selected because of their high susceptibility to leishmania and the progressive, nonhealing nature of their lesions due to the inability of their immune systems to mount an effective cellular response. Most other mammalian species, including humans and C3He mice develop an immune response which serves to increase the efficacy of the antileishmanial agents.

Mice weighed approximately 20 grams, were 8–12 weeks old, and individually ear-tagged. The hair near the base of the tail of each experimental animal was clipped. On day one the bare skin was inoculated with 5–20 million Leishmania (stationary phase) promastigotes of the appropriate species. After 60 days, an ulcerated lesion approximately 50 mm square developed. Ten and 30 mice were assigned to the control and test groups, respectively. From day 61 to day 70 the animals were treated with the formulation. Some animals were treated twice daily for ten days. Some animals infected with *L. major* were also treated two times daily for two days or one time daily for five days. The mice in the control groups were treated with the carrier without the paromomycin and gentamicin. The formulation of the invention tested contained 15% paromomycin and 0.5% gentamicin. For comparison, a formulation of El-On containing 15% paromomycin and 12% methylbenzethonium chloride in white soft paraffin were also tested. The dosages administered to the individual animal depended on the size of the lesions as shown in the table below:

TABLE I

Dosage applied to Lesions based on Lesion Area

| Lesion Area | Dosage | Lesion Area | Dosage |
|---|---|---|---|
| 400 sq. mm | 0.2 ml | 20–30 sq. mm | 0.02 |
| 200–300 | 0.1 | 10–15 | 0.01 |
| 75–150 | 0.05 | 1–6 | 0.001 |
| 40–50 | 0.03 | | |

The drug efficacy was determined based on three criteria: (a) the area of the lesion after the termination of treatment (b) the number of viable amastigotes per gram of lesion after termination of treatment, and (c) the number of animals healed/the number tested. Animals were considered clinically healed when lesions were completely resolved, the skin was normal and there was hair growth. The animals were considered clinically cured when the skin and hair growth remained normal for at least 70 days after beginning of treatment whether or not parasites could be detected in the skin. Animals having normal skin with hair growth in which no viable amastigotes were detected were considered parasitically cured. To determine the number of viable amastigotes per gram of lesion required sacrificing the animals. The viable amastigotes were measured using fluorescein diacetate-ethyl benzine staining.

The actual formulation used contained the following:

| | | | |
|---|---|---|---|
| Paromomycin sulfate | 15% | gentamicin sulfate | 0.5% |
| Aquaphilic/10% urea | 67.8% | distilled water: | 16.7% |

The Aquaphilic components as disclosed by the manufacturer are:

| | | | |
|---|---|---|---|
| sorbitol | 4% | lactic acid | 0.5% |
| distilled water: | 39.85% | propylene glycol | 6% |
| sodium lauryl sulfate | 0.75% | isopropyl palmitate | 0.5% |
| stearyl alcohol | 19.0% | white petrolatum | 19.0% |
| propyl paraben | 0.15% | methyl paraben | 0.25% |

The Aquaphilic was formulated then with urea before formulation with the antileishmanial agents.

Example 1

Thirty Balb/c mice were infected with $5 \times 10^6$ stationary phase *L. major* promastigotes at the base of the tail on day 1. On day 61 treatment was commenced using a composition containing 15% paromomycin and 0.5% gentamicin which was applied topically twice daily for ten days. The effect on the lesion area was measured. The lesion area on controls was approximately 80 mm at day 61 and increased thereafter to about 300 mm by day 105. The treated animals had no lesions at day 105 (45 days after treatment), though one animal showed a small lesion resulting from metastasis 80 days after treatment ceased (day 140). The number of amastigotes per gram of lesion was determined. At day 60, there were about 35 million amastigotes per gram lesion in the controls and about 45 million amastigotes per gram of lesion in the animals that then commenced treatment. At the end of the treatment period, no amastigotes were found in the lesions of the treated animals. The animals remained free of amastigotes until the end of the test period which ended 70 days after cessation of treatment (day 150). The untreated animals had sever infection with 120 million amastigotes by day 105 when the animals were sacrificed.

Example 2

The test above was repeated treating the animals with the compositions of El-On instead of the compositions of the invention. In this instance, the animals continued to have a drop in lesion area until day 30, when lesions appeared healed. However, thirty days after treatment lesions began to appear in some of the animals, and at 60 days after treatment 5 of the surviving 28 animals had lesions. The more important difference was in the number of viable amastigotes per gram of lesion. After 45 days post treatment the number of amastigotes seen in the lesions of the animals treated with the compositions of El-On was about ⅓=0 the number of amastigots per gram of lesion as seen in the untreated animals.

Example 3

The preferred compositions of El-On were compared with the compositions of the invention and were tested against several strains of Leishmania in the manner described above. The data is seen in Table II. Test I refers to the preferred composition of El-On containing 15% paromomycin and 12% methyl-benzenthionium Chloride while Test II refers to the composition of the invention containing 15% paromomycin and 0.5% gentamicin. Drug efficacy is given as # of mice healed/# of mice tested.

TABLE II

| Days post treatment | Control | *L. Major* I | II | *L. Mexicana* I | II | *L. panamensi* I | II | *L. amazonensis* I | II |
|---|---|---|---|---|---|---|---|---|---|
| 0 | 0/30 | 0/30 | 0/30 | 0/30 | 0/30 | 0/30 | 0/30 | 0/30 | 0/30 |
| 10 | 0/30 | 21/30 | 28/30 | 24/30 | 28/30 | 3/30 | 24/10 | 4/30 | 19/30 |
| 20 | 0/30 | 27/30 | 30/30 | 30/30 | 30/30 | 25/30 | 30/30 | 9/30 | 30/30 |
| 30 | 0/30 | 29/29 | 29/29 | 30/30 | 30/30 | 14/30 | 30/30 | 11/30 | 30/30 |
| 40 | 0/30 | 27/29 | 29/29 | 30/30 | 30/30 | 12/30 | 30/30 | 3/30 | 30/30 |
| 50 | D or S | 27/28 | 29/29 | 30/30 | 30/30 | 7/30 | 30/30 | 0/29 | 30/30 |
| 60 | | 26/28 | 29/29 | 27/30 | 30/30 | 6/30 | 29/29 | 0/27 | 30/30 |
| 70 | | 23/28 | 29/29 | 25/30 | 30/30 | 0/30 | 29/29 | 0/27 | 30/30 |
| 80 | | S | 28/29 | 25/30 | 30/30 | S | S | S | S |
| 90 | | | 28/29 | S | S | | | | |

D = Dead, S = Sacrificed

Example 3

The synergistic effect was shown in a test using three compositions: paromomycin 15% alone (I), gentamicin 0.5% alone (II) and a combination paromomycin 15% with gentamicin 0.5% (III). Results are reported as # of mice healed/# mice tested. Days are numbered from before or after treatment was initiated.

TABLE III

| Day | Control | Comp. I | Comp. II | Comp. III |
|---|---|---|---|---|
| −10 | 0/10 | 0/10 | 0/10 | 0/10 |
| 0 | 0/10 | 0/10 | 0/10 | 0/10 |
| 7 | 0/10 | 5/10 | 1/10 | 7/10 |
| 14 | 0/10 | 6/10 | 0/10 | 10/10 |
| 30 | 0/10 | 6/10 | 0/10 | 10/10 |
| 60 | 0/10 | 2/10 | 0/10 | 10/10 |
| 70 | 0/10 | 1/10 | 0/10 | 10/10 |

From the above data it is clear that the use of paromomycin with the gentamicin results in unexpected and beneficial synergistic action. Further, the area of scarring using the combination product was considerably less.

Example 4

The combination compositions of the invention were tested in the hamster model using *L. donovani,* an organisms which causes visceral leishmaniasis in this animal model. The response to treatment with gentamicin, paromomycin, and with the combination of the invention was compared.

TABLE IV

| Active agent dosage mg/kg | % suppression | Mean # organisms |
|---|---|---|
| paromomycin[a] | | |
| 1400 | 53 | 696 |
| 900 | 42 | 857 |
| 700 | 36 | 954 |
| 500 | 36 | 945 |
| gentamicin[b] | | |
| 700 | 24 | 1128 |
| paromomycin/ gentamicin[c] | | |
| 1400 | 63 | 551 |
| 900 | 55 | 664 |
| 700 | 52 | 709 |
| 500 | 48 | 771 |
| Glucantime | | |
| 208 | 64 | 528 |
| 52 | 32 | 1010 |
| 26 | 11 | 1329 |
| Control | 0 | 1487 |

The antimonial, Glucantime was given at usual doses which are acceptable for therapy by injection in hospital.

The compositions were tested on both an immune suppressed model (Balb/c mice) and a healing model (hamsters). Both models responded well to the combination compositions. The compositions of the invention resulted in more rapid closing of lesions, more permanent healing and considerably improved cosmetic results compared to prior art compounds.

What is claimed is:

1. A leishmania-inhibiting pharmaceutical composition of matter comprising an antileishmania-effective amount of paromomycin of 10% to 40% or a pharmaceutically acceptable salt thereof and an paromomycin-potentiating effective amount of gentamicin of 0.2% to 5%, or a pharmaceutically acceptable salt thereof in a pharmaceutically effective carrier.

2. A composition of claim 1 in a emulsion base.

3. A composition of claim 1 wherein the carrier contains alcohols, non-toxic glycols and petrolatum.

4. A composition of claim 1 further containing a penetrant.

5. A composition of claim 4 wherein the penetrant is urea.

6. A composition of claim 1 further containing a preservative.

7. A composition of claim 3 containing urea and, additionally, sorbitol, propylene glycol, lactic acid, sodium lauryl sulfate, isopropyl palmitate, stearyl alcohol, white petrolatum, propyl paraben, and methyl paraben.

8. A composition of claim 7 containing 15% paromomycin sulfate and 0.5% gentamicin sulfate.

9. A method of ameliorating the effect of leishmaniasis comprising administration of a composition of claim 1 to a patient suffering from leishmaniasis.

10. A method of claim 9 wherein the leishmaniasis results from infection with a New World strain of Leishmania.

11. A method of claim 9 wherein the leishmaniasis results from infection with an Old World strain of Leishmania.

12. A method of claim 9 wherein the composition of claim 1 is administered twice daily for at least two consecutive days.

13. A method of treating leishmaniasis comprising topical administration of a composition of claim 1 to a patient suffering from leishmaniasis.

14. A method of claim 9 wherein the composition is administered topically.

* * * * *